(12) United States Patent
Selvarajan et al.

(10) Patent No.: US 9,981,105 B2
(45) Date of Patent: May 29, 2018

(54) ELBOW ASSEMBLY

(71) Applicant: ResMed Limited, Bella Vista (AU)

(72) Inventors: Karthikeyan Selvarajan, Thronleigh (AU); Christopher Scott Skipper, West Ryde (AU); Joshua Adam Gudiksen, Mortdale (AU); Steven John Lubke, Stanmore (AU); Alison Oldenburg, Crows Nest (AU); Murray William Lee, Quakers Hill (AU)

(73) Assignee: ResMed Limited, Bella Vista (AU)

( * ) Notice: Subject to any disclaimer, the term of this patent is extended or adjusted under 35 U.S.C. 154(b) by 151 days.

(21) Appl. No.: 13/950,362

(22) Filed: Jul. 25, 2013

(65) Prior Publication Data
US 2013/0306066 A1     Nov. 21, 2013

Related U.S. Application Data

(63) Continuation of application No. 13/617,194, filed on Sep. 14, 2012, now Pat. No. 8,517,024, which is a
(Continued)

(51) Int. Cl.
*A61M 16/08*     (2006.01)
*A61M 16/06*     (2006.01)
*A61M 16/20*     (2006.01)

(52) U.S. Cl.
CPC ........ *A61M 16/0816* (2013.01); *A61M 16/06* (2013.01); *A61M 16/0633* (2014.02);
(Continued)

(58) Field of Classification Search
CPC .. A61M 16/0816; A61M 16/06; A61M 16/08; A61M 16/20; A61M 16/0633; A61M 16/0825; A61M 16/0683; A61M 16/208
(Continued)

(56) References Cited

U.S. PATENT DOCUMENTS 3,796,216 A    3/1974  Schwarz
5,438,981 A    8/1995  Starr et al.
(Continued)

FOREIGN PATENT DOCUMENTS

EP          1525895         4/2005
WO    PCT/AU97/000849      12/1997
(Continued)

OTHER PUBLICATIONS

International Search Report for PCT/AU2007/000836 (dated Jul. 11, 2007) (4 pages).
(Continued)

*Primary Examiner* — Todd J Scherbel
*Assistant Examiner* — Elliot S Ruddie
(74) *Attorney, Agent, or Firm* — Nixon & Vanderhye P.C.

(57) ABSTRACT

An elbow assembly for a mask system includes an elbow including a slot and a port, an anti-asphyxia valve adapted to be received within the slot and including a flap portion adapted to selectively close the port depending on the presence of pressurized gas, and a support member to secure the anti-asphyxia valve to the elbow. The support member includes a slot that is adapted to interlock with a protrusion provided to the anti-asphyxia valve.

28 Claims, 17 Drawing Sheets

Related U.S. Application Data continuation of application No. 12/308,471, filed as application No. PCT/AU2007/000836 on Jun. 15, 2007, now Pat. No. 8,342,181.

(60) Provisional application No. 60/814,055, filed on Jun. 16, 2006, provisional application No. 60/858,699, filed on Nov. 14, 2006.

(52) U.S. Cl.
CPC .... *A61M 16/0683* (2013.01); *A61M 16/0825* (2014.02); *A61M 16/20* (2013.01)

(58) Field of Classification Search
USPC ............ 128/202.22, 202.27, 205.24, 205.25, 128/206.21, 207.12, 207.13
See application file for complete search history.

(56) References Cited

U.S. PATENT DOCUMENTS

| | | | |
|---|---|---|---|
| 5,465,712 A | 11/1995 | Malis et al. | |
| 5,647,355 A | 7/1997 | Starr et al. | |
| D558,333 S * | 12/2007 | Hitchcock et al. ... | A61M 16/06 D24/110.1 |
| 8,136,524 B2 | 3/2012 | Ging et al. | |
| 2002/0153012 A1 | 10/2002 | Gunaratnam et al. | |
| 2002/0174867 A1 | 11/2002 | Gunaratnam et al. | |
| 2003/0005931 A1 * | 1/2003 | D. Jaffre ............... | A61M 16/08 128/204.18 |
| 2003/0196656 A1 | 10/2003 | Moore et al. | |
| 2003/0196657 A1 * | 10/2003 | Ging ..................... | A61M 16/06 128/201.22 |
| 2004/0094157 A1 * | 5/2004 | Dantanarayana et al. ........................ | 128/206.21 |
| 2004/0112385 A1 | 6/2004 | Drew | |
| 2004/0255948 A1 | 12/2004 | Smith et al. | |
| 2009/0065729 A1 | 3/2009 | Worboys et al. | |
| 2010/0236549 A1 | 9/2010 | Selvarajan et al. | |
| 2013/0008439 A1 | 1/2013 | Selvarajan et al. | |

FOREIGN PATENT DOCUMENTS

| | | |
|---|---|---|
| WO | WO 2000/038772 | 7/2000 |
| WO | WO 02/051486 A1 | 7/2002 |
| WO | WO 02/096342 A2 | 12/2002 |
| WO | WO 02096342 A2 * | 12/2002 |
| WO | PCT/AU2004/001832 | 12/2004 |
| WO | WO 2005/063326 | 7/2005 |
| WO | PCT/AU2006/000031 | 1/2006 |
| WO | PCT/AU2006/000770 | 6/2006 |
| WO | WO 2006/122369 A1 | 11/2006 |

OTHER PUBLICATIONS

International Search Report for PCT/AU2006/000031, dated Mar. 28, 2006 (6 pages).
European Search Report issued in EP Appln. No. 06704169.9, dated Mar. 4, 2010, 7 pgs.
Office Action dated Mar. 28, 2011 in European Application No. 06 704 169.9 (5 pages).
Third Party Observations dated Mar. 25, 2011 in European Application No. 06 704 169.9 (2 pages).

* cited by examiner

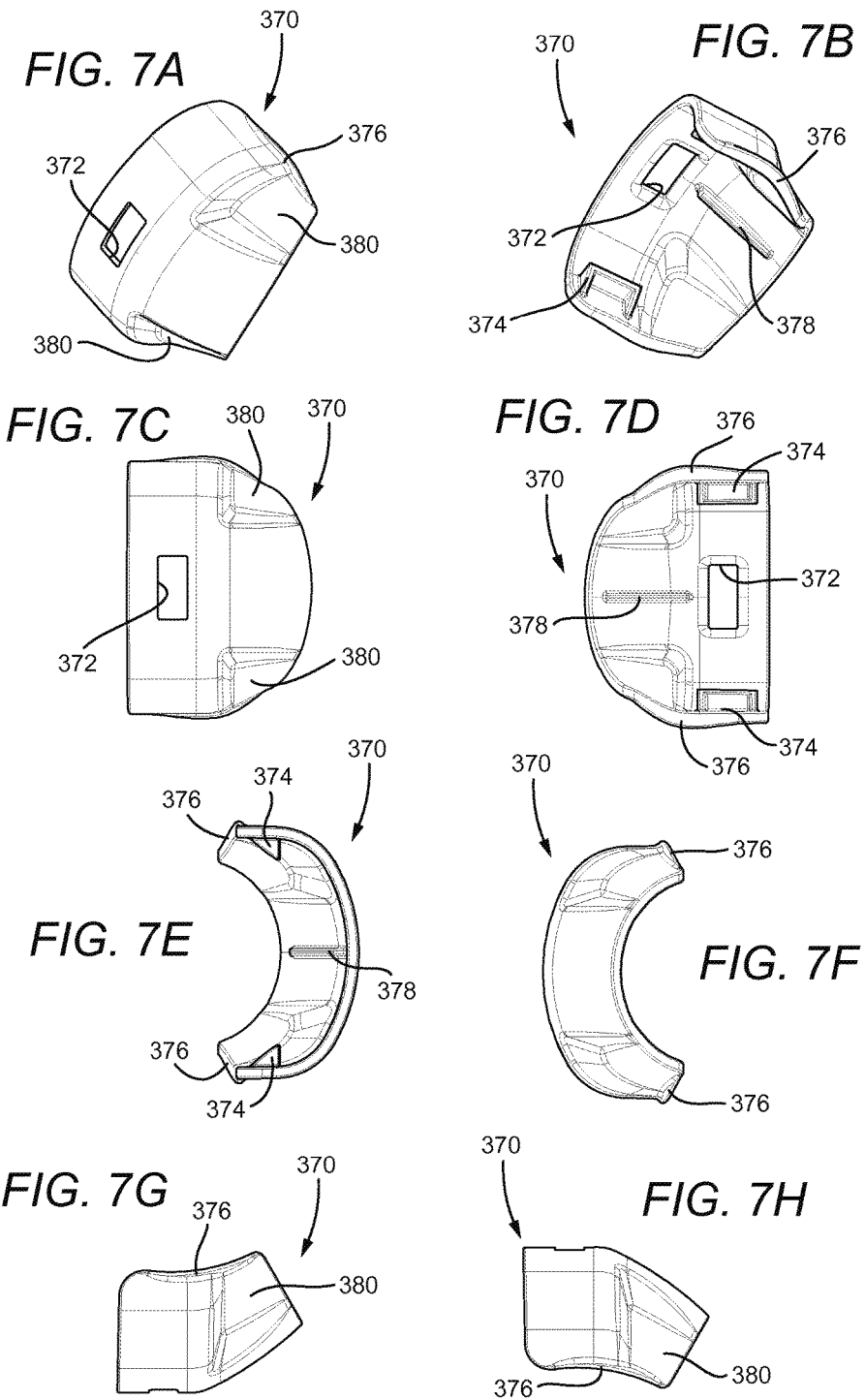

ELBOW ASSEMBLY

CROSS-REFERENCE TO APPLICATIONS

This application is a continuation of Ser. No. 13/617,194, filed Sep. 14, 2012, now allowed, which is a continuation of U.S. Ser. No. 12/308,471, filed Dec. 16, 2008, now U.S. Pat. No. 8,342,181, which is the U.S. national phase of International Application No. PCT/AU2007/000836, filed Jun. 15, 2007, which designated the U.S. and claims the benefit of U.S. Provisional Application Nos. 60/814,055, filed Jun. 16, 2006, and 60/858,699, filed Nov. 14, 2006, each of which is incorporated herein by reference in its entirety.

Also, PCT Application No. PCT/AU2006/000031, filed Jan. 12, 2006, which claims priority to U.S. Provisional Application No. 60/726,699, and PCT Application No. PCT/AU2006/000770, filed Jun. 6, 2006, which claims priority to U.S. Provisional Application Nos. 60/687,453, 60/702,582, and 60/795,562, are each incorporated herein by reference in its entirety.

FIELD OF THE INVENTION

The present invention relates to an elbow assembly for use with a mask assembly used for treatment, e.g., of Sleep Disordered Breathing (SDB) with Continuous Positive Airway Pressure (CPAP) or Non-Invasive Positive Pressure Ventilation (NPPV).

BACKGROUND OF THE INVENTION

A mask assembly typically includes a relatively rigid shell, e.g., a frame, and a patient interface, e.g., a pair of nozzles (which may be in the form of nasal pillows, nasal prongs, cannulae, or nasal puffs) or a cushion (nasal or full-face), that is supported by the rigid shell and structured to deliver pressurized gas to the patient or user in a comfortable, sealed manner. The mask assembly is usually held in place using a headgear assembly.

In some applications, there may be a clinical requirement to provide the mask assembly with one or more safety devices, such as means for $CO_2$ washout, vents, anti-asphyxia valves and the like. In some cases, these additional components are assembled between the gas delivery conduit and the mask assembly. Problems with prior art assemblies may include:

(a) inadvertent assembly without one or more of the safety devices;

(b) incorrect assembly/alignment; and/or (c) incorrect re-assembly following inadvertent dis-assembly during the course of treatment.

Flow generators typically deliver pressurized breathable gas (air) to a patient wearing the mask assembly. In CPAP treatment, gas is delivered to the patient's airways at about 2-30 cm $H_2O$ above atmospheric pressure. The flow generator is generally connected to flexible tubing (air delivery tube) that is secured to the mask assembly worn by the patient. If the flow generator's operation is interrupted as a result of power outage or other mechanical/electrical failure, there may be a significant build up of carbon dioxide in the mask as the patient's exhaled air is not washed out of outlet vents that are usually provided to the mask assembly. This may present a health risk to the patient.

Several patents have addressed this risk, e.g., by use of a safety valve for gas or air delivery mask assemblies. See, e.g., U.S. Pat. No. 3,796,216 to Schwarz, and U.S. Pat. No. 5,438,981 to Starr et al., as well as PCT international application no. PCT/AU97/00849.

SUMMARY OF THE INVENTION

One aspect of the present invention relates to an elbow assembly for a mask system including an elbow including a slot and a port, an anti-asphyxia valve adapted to be received within the slot and including a flap portion adapted to selectively close the port depending on the presence of pressurized gas, and a support member to secure the anti-asphyxia valve to the elbow. The support member includes a slot that is adapted to interlock with a protrusion provided to the anti-asphyxia valve. The support member includes wings. The wings are structured such that the wings protrude outwardly from the elbow when the support member is secured to the elbow.

Another aspect of the present invention relates to an elbow assembly for a mask system including an elbow including a slot and a port, an anti-asphyxia valve adapted to be received within the slot and including a flap portion adapted to selectively close the port depending on the presence of pressurized gas, and a support member to secure the anti-asphyxia valve to the elbow. The support member includes a slot that is adapted to interlock with a protrusion provided to the anti-asphyxia valve. The slot of the support member is sized to prevent assembly of the flap portion of the anti-asphyxia valve through the slot of the support member.

Another aspect of the present invention relates to an elbow assembly for a mask system. The elbow assembly includes an elbow including a slot and a port, an anti-asphyxia valve adapted to be received within the slot and including a flap portion adapted to selectively close the port depending on the presence of pressurized gas, and a support member to secure the anti-asphyxia valve to the elbow. The support member includes a slot that is adapted to interlock with a protrusion provided to the anti-asphyxia valve. The support member includes one or more portions that have a textured or frosted surface.

It will of course be understood that the structural and/or functional features of the present invention may be usefully employed in full facial masks or nasal masks or nasal prongs, nozzles, nare seals, and/or cannulae.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 7A to 7H show various views of a support member of the elbow assembly shown in FIGS. 5A to 5I;

DETAILED DESCRIPTION OF ILLUSTRATED EMBODIMENTS

Figure 1:
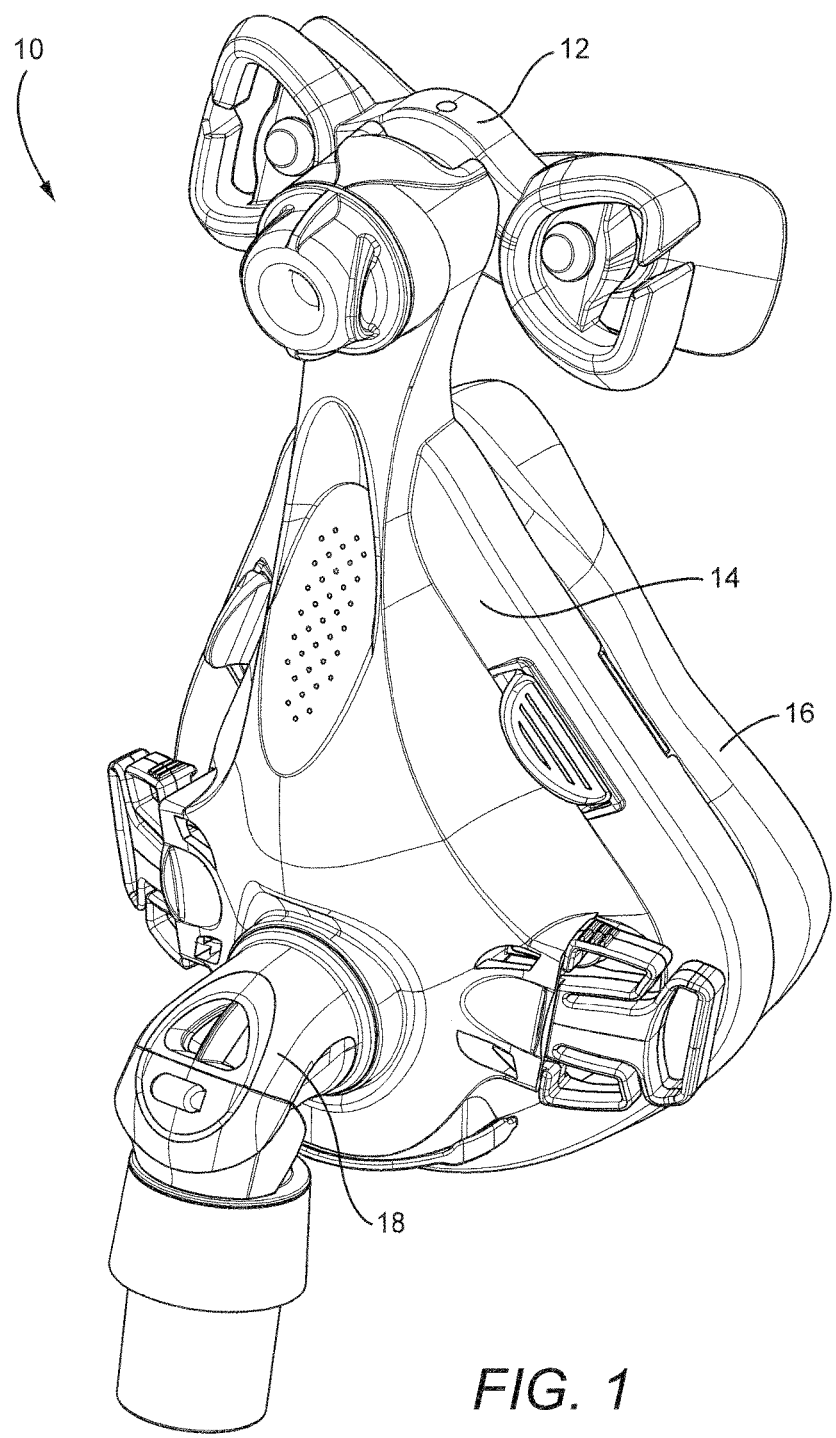
FIG. 1 shows an exemplary embodiment of a full facial mask assembly.

FIG. 1 illustrates an exemplary embodiment of a full facial mask assembly ("FMA") 10. As illustrated, the mask assembly 10 includes a frame 14, a cushion 16 provided to the frame 14 and adapted to form a seal with the patient's face, an elbow assembly 18 provided to the frame 14 and adapted to be connected to an air delivery tube that delivers breathable gas to the patient, and a forehead support 12 to provide a support and stability mechanism between the mask assembly 10 and the patient's forehead. A headgear assembly (not shown) may be removably attached to the frame 14 (e.g., via headgear clips) and the forehead support 12 to maintain the mask assembly 10 in a desired adjusted position on the patient's face.

Further details and embodiments of such mask assemblies are disclosed in PCT Application No. PCT/AU2006/000031, the entirety incorporated herein by reference.

1. First Illustrated Embodiment of Elbow Assembly

FIGS. 2A to 2H illustrate an elbow assembly 218 according to an embodiment of the present invention. In the illustrated embodiment, the elbow assembly 218 is adapted for use with a mask assembly of the type described above in FIG. 1. However, the elbow assembly 218 may be implemented into other mask systems, e.g., full-face mask, mouth mask, or a nasal mask.

The main components of the elbow assembly 218 are an elbow 230 (see FIGS. 3A to 3F), an anti-asphyxia valve (AAV) 250 (see FIGS. 8A to 8G), and a support member 270 (see FIGS. 4A to 4J) to secure the AAV 250 to the elbow 230. It is noted that the AAV 250 is a common component that may be used in the elbow assembly 218 as well as an elbow assembly 318 described in greater detail below.

1.1 Elbow

As shown in FIGS. 3A to 3F, the elbow 230 includes a first portion 232 provided to a mask frame and a second portion 234 provided to a swivel joint connected to an air delivery tube. The first portion 232 includes snap-fit tabs 233, e.g., six tabs, to connect the first portion 232 to the mask frame with a snap-fit. However, more or less snap-fit tabs may be used, e.g., 2-10 tabs.

The second portion 234 includes snap-fit tabs 235, e.g., six tabs, to connect the second portion 234 to the swivel joint. The snap-fit diameter at the second portion 234 may be smaller than the snap-fit diameter at the first portion 232 to prevent incorrect assembly. Annular rings 236, e.g., three rings, are provided on the second portion 234 for improved seal with the swivel joint and improved manufacturability.

The elbow 230 also includes a slot 238 to receive the AAV 250, a port 240 that is selectively closed by the flap portion 252 of the AAV (depending on the presence of pressurized gas), and two tabs 242 for attaching the support member 270 with a snap-fit. As illustrated, the port 240 has a central rib 241 to prevent small objects from falling in or being placed in the port 240 and thereby affecting AAV function.

Figure 2A:
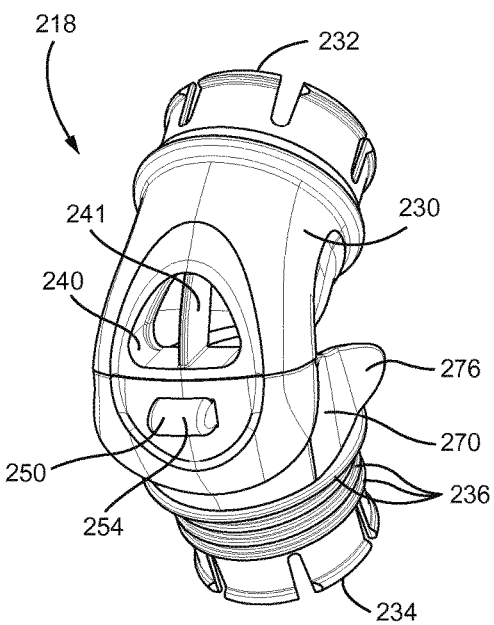
FIGS. 2A to 2H show various views of an elbow assembly according to an embodiment of the present invention.
Figure 2B:
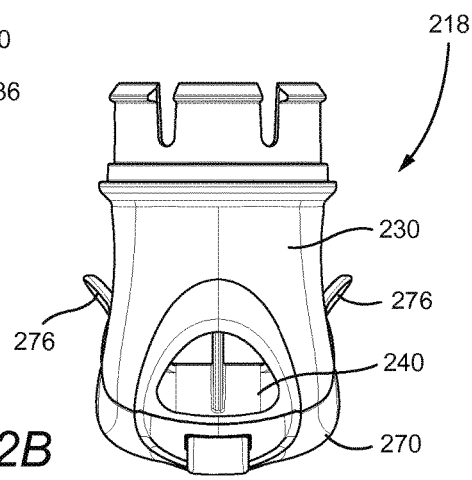
Figure 2C:
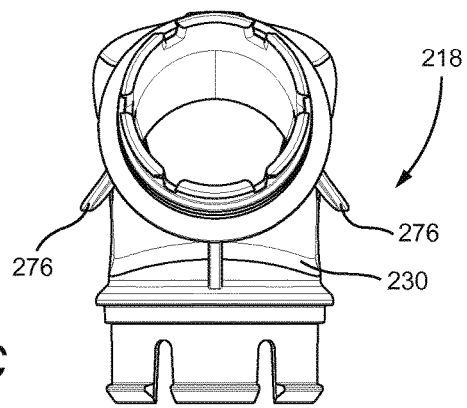
Figure 2D:
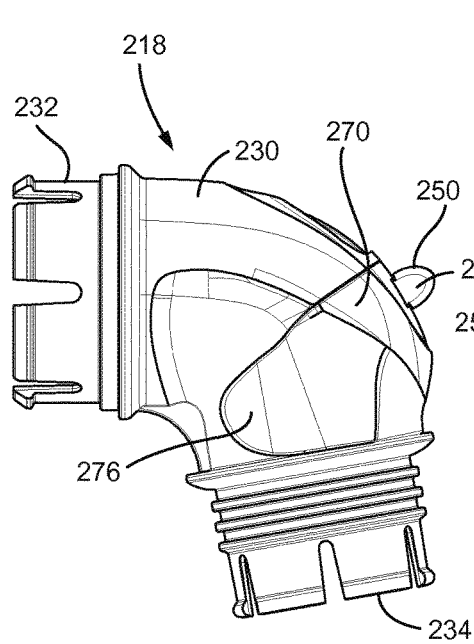
Figure 2E:
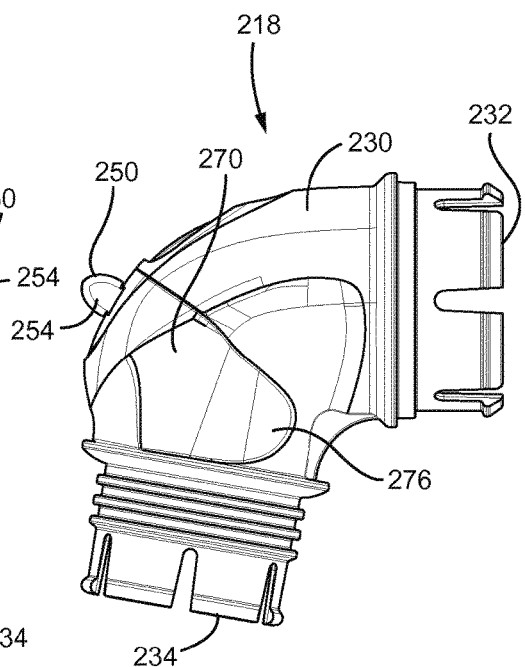
Figure 2F:
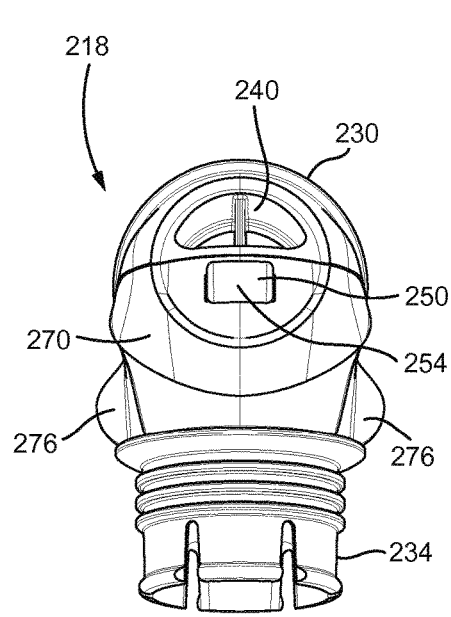
Figure 2G:
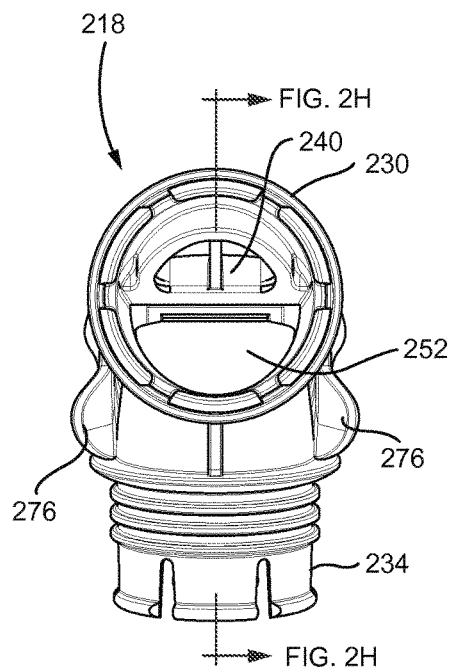
Figure 2H:
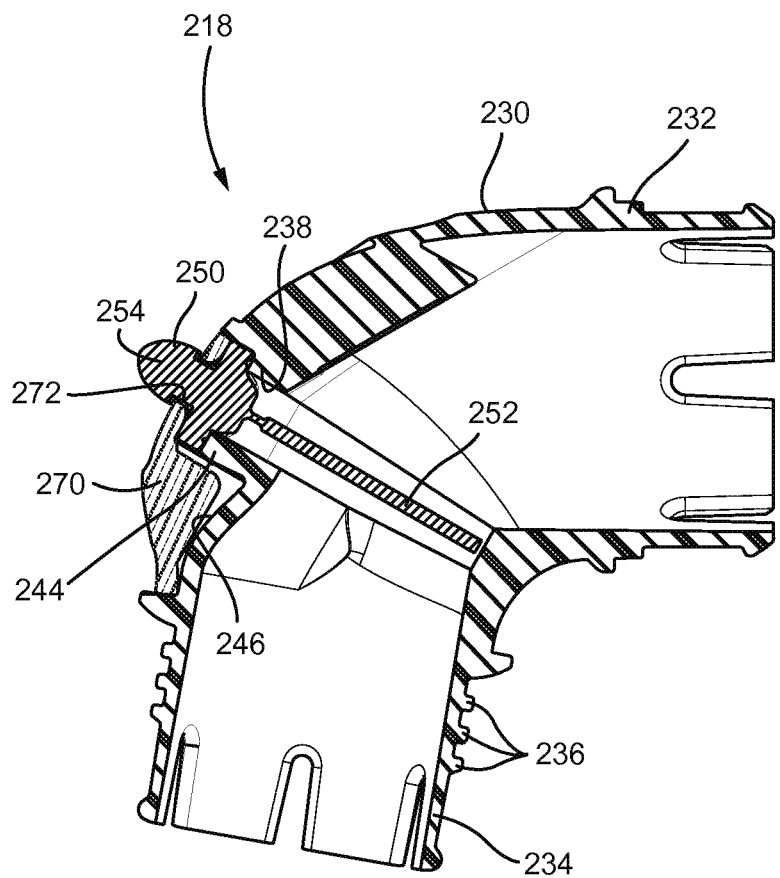
Figure 3A:
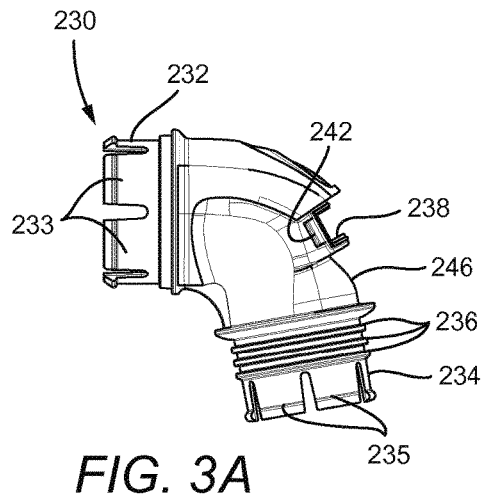
FIGS. 3A to 3F show various views of an elbow of the elbow assembly shown in FIGS. 2A to 2H.
Figure 3B:
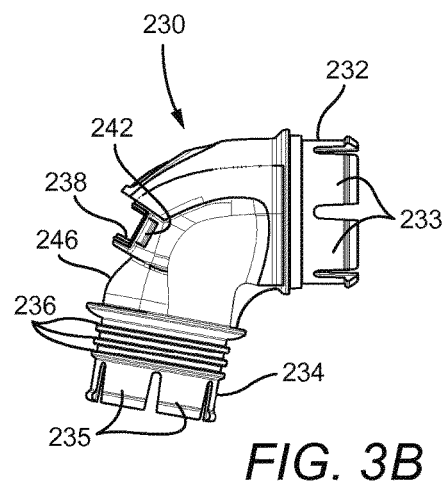
Figure 3C:
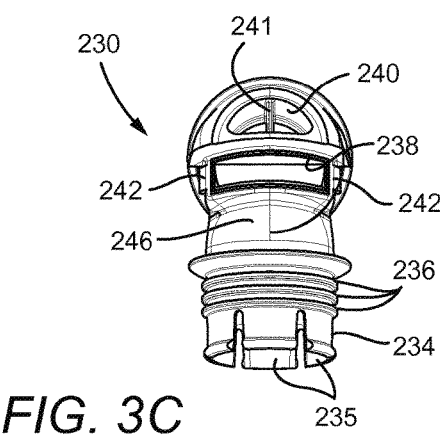
Figure 3D:
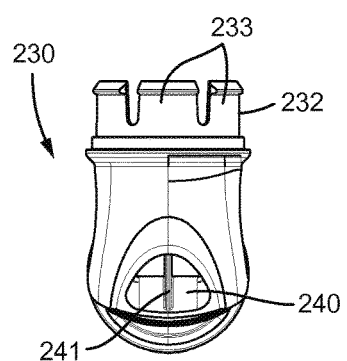
Figure 3E:
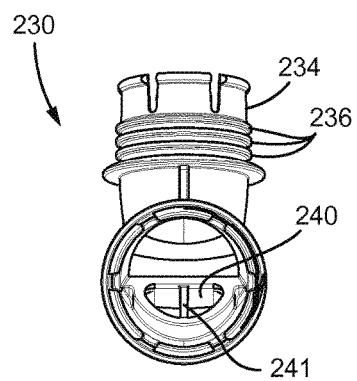
Figure 3F:
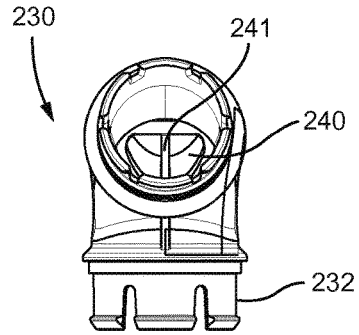
Figure 4A:
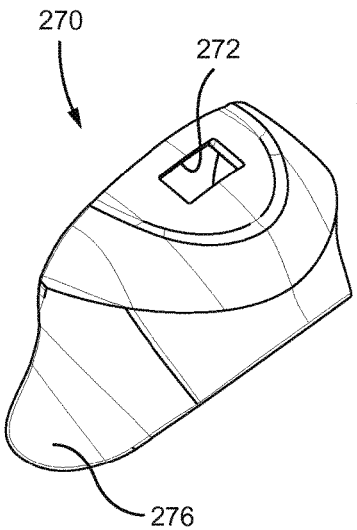
FIGS. 4A to 4J show various views of a support member of the elbow assembly shown in FIGS. 2A to 2H.
Figure 4B:
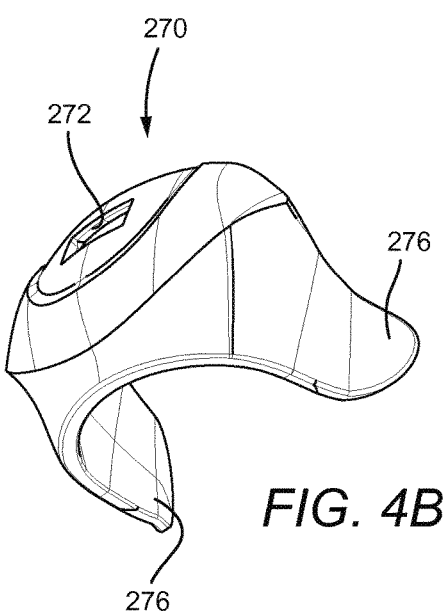
Figure 4C:
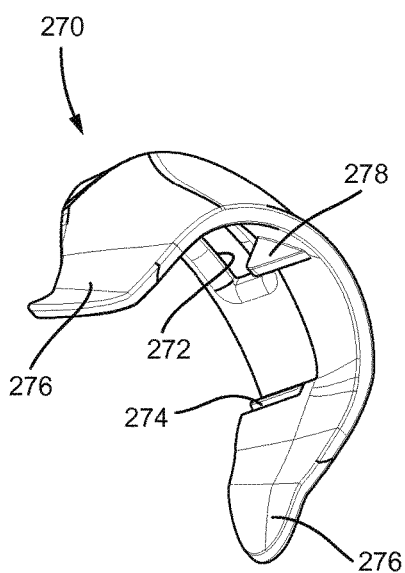
Figure 4D:
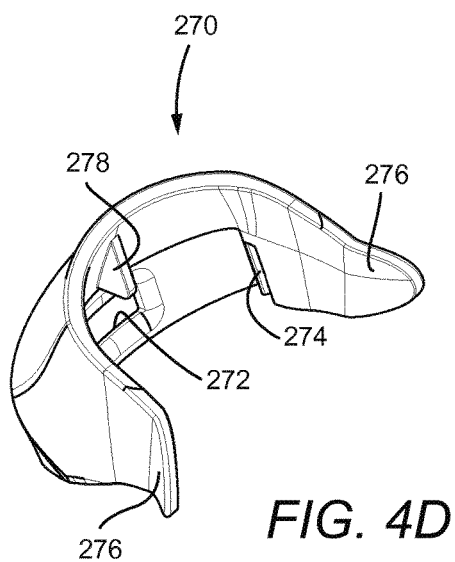
Figure 4E:
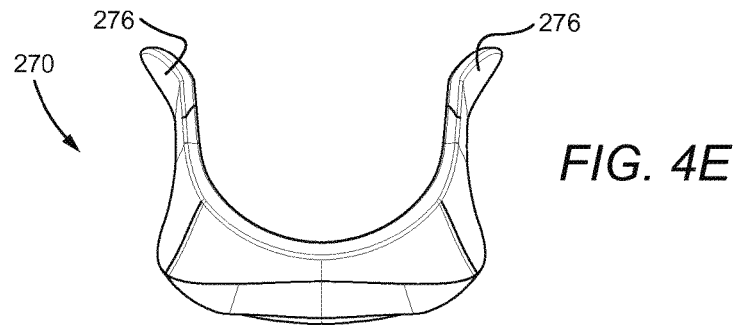
Figure 4F:
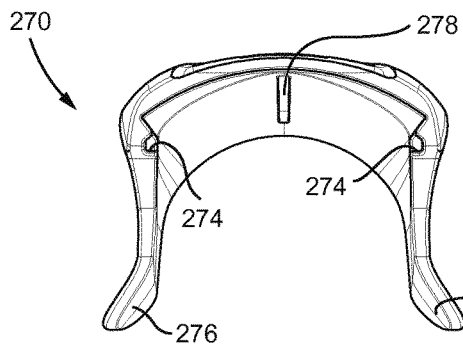
Figure 4G:
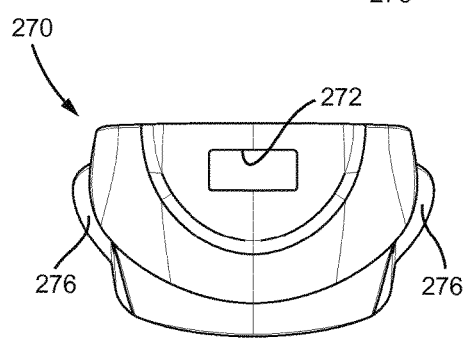
Figure 4H:
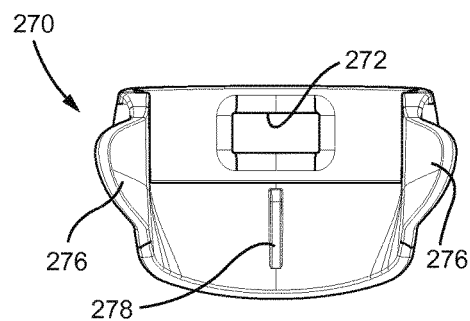
Figure 4I:
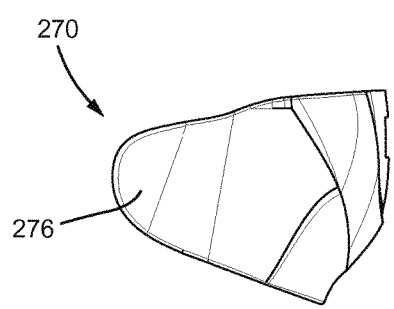
Figure 4J:
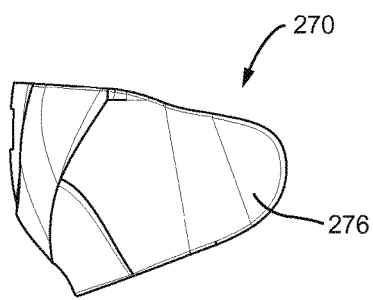
Figure 5A:
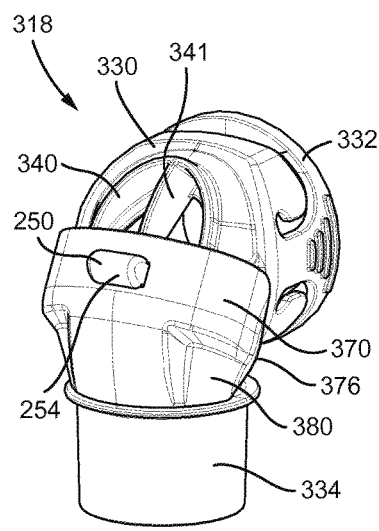
FIGS. 5A to 5I show various views of an elbow assembly according to another embodiment of the present invention.
Figure 5B:
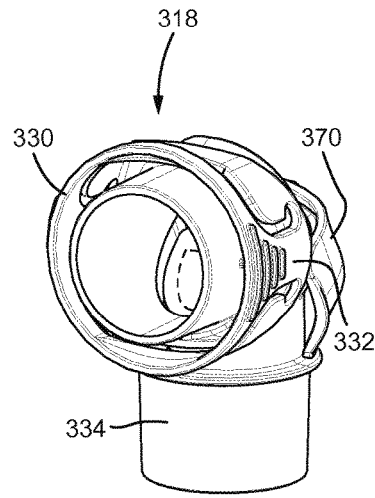
Figure 5C:
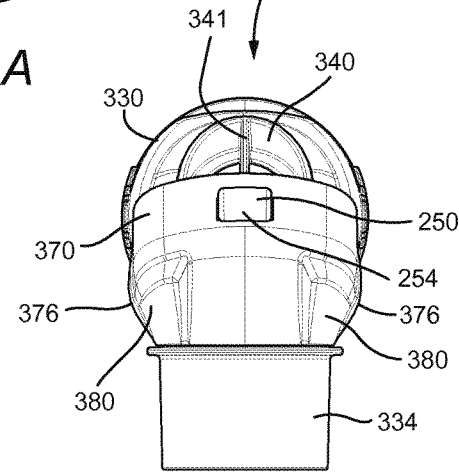
Figure 5D:
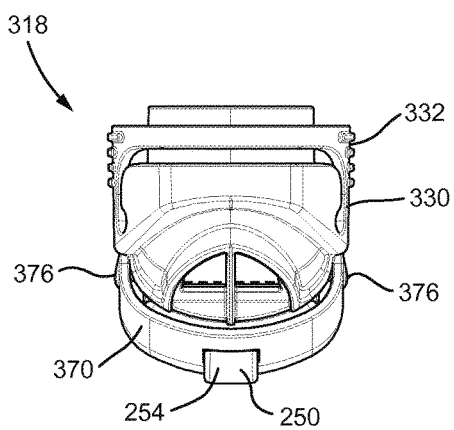
Figure 5E:
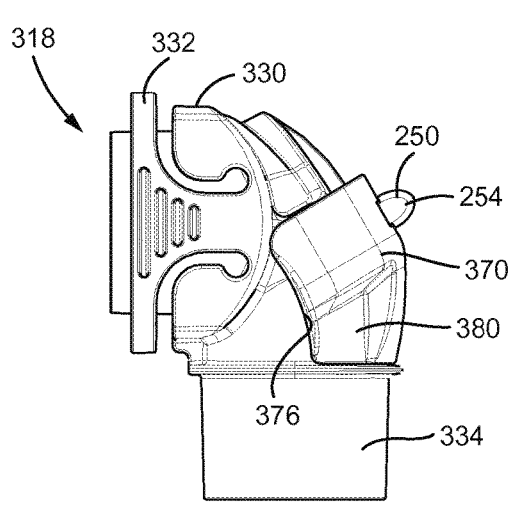
Figure 5F:
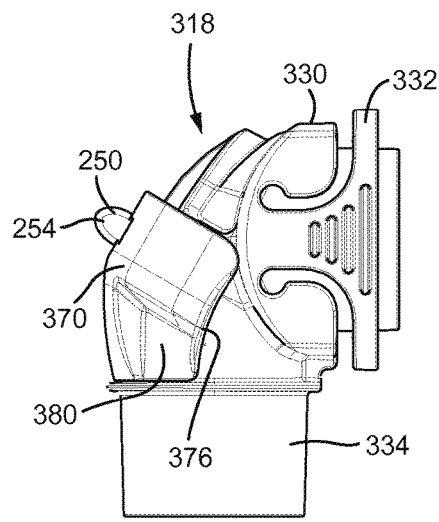
Figure 5G:
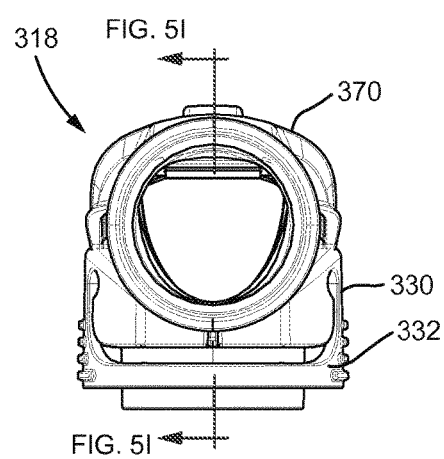
Figure 5H:
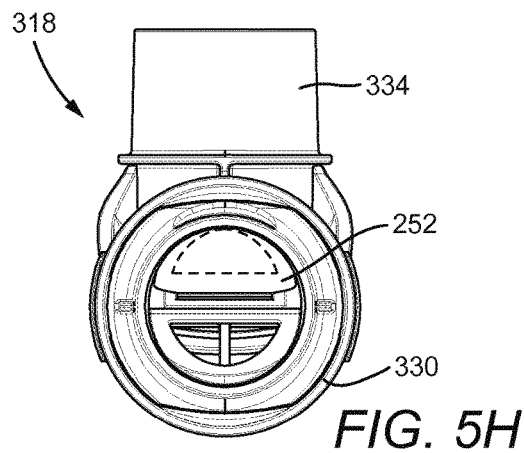
Figure 5I:
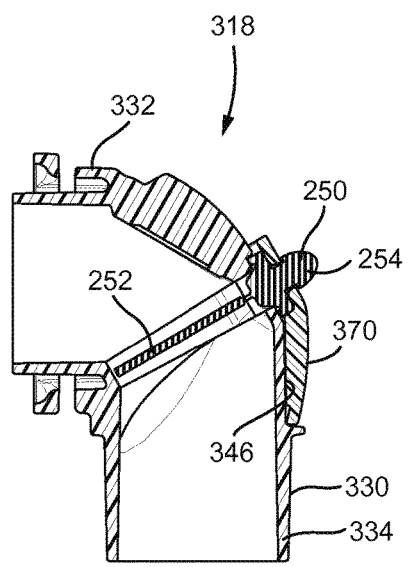
Figures 6A, 6B:
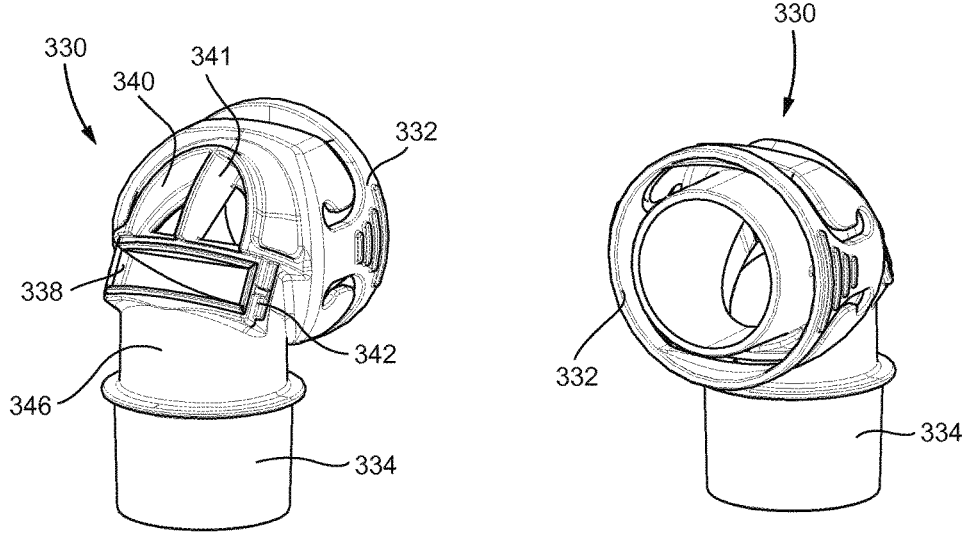
FIGS. 6A to 6H show various views of an elbow of the elbow assembly shown in FIGS. 5A to 5I.
Figure 6C:
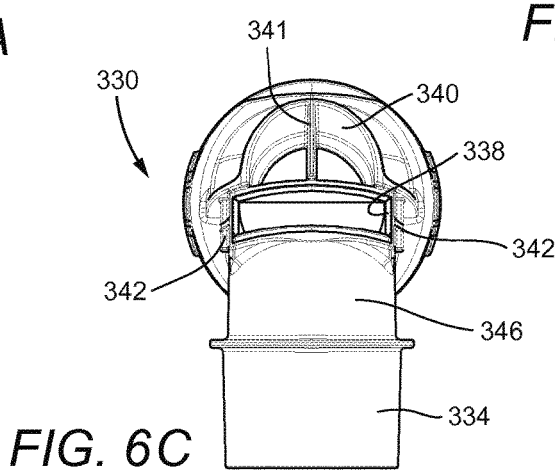
Figure 6D:
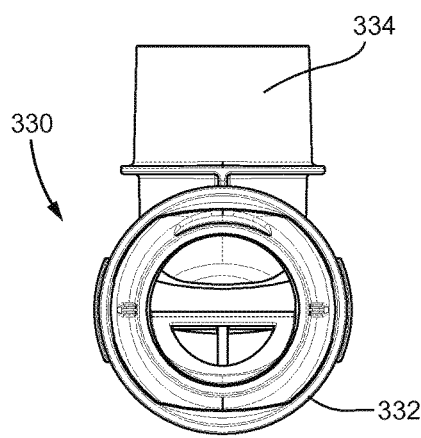
Figure 6E:
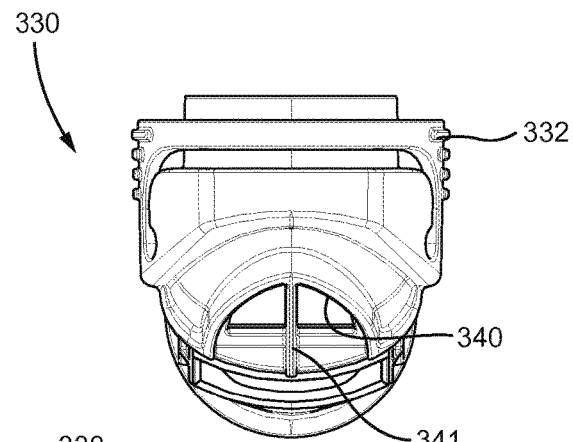
Figure 6F:
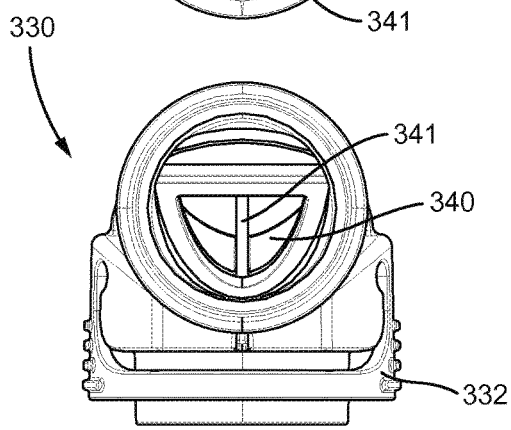
Figures 6G, 6H:
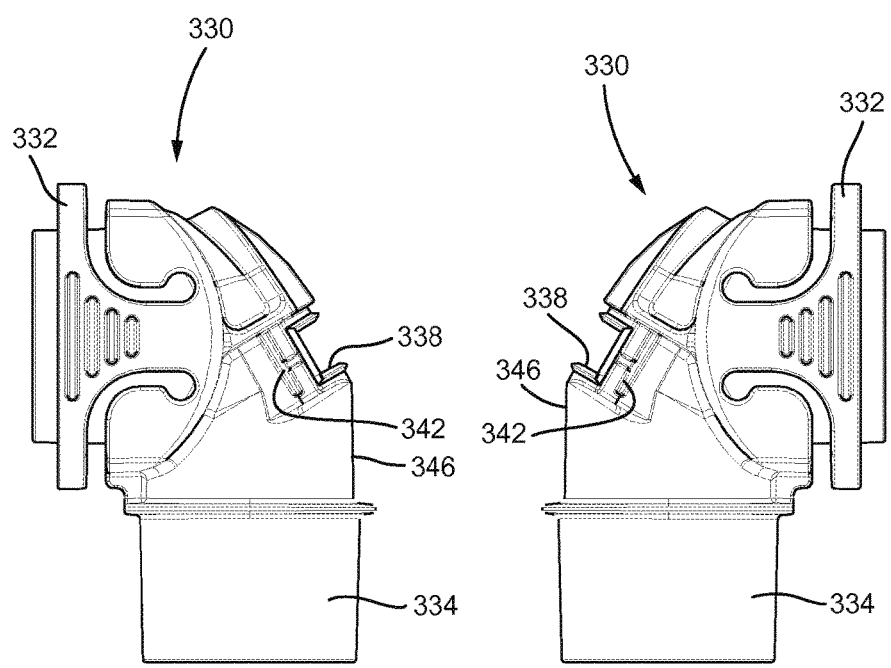
Figure 8A:
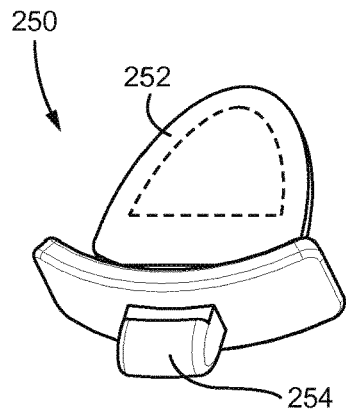
FIGS. 8A to 8G show various views of an anti-asphyxia valve (AAV) according to an embodiment of the present invention.
Figure 8B:
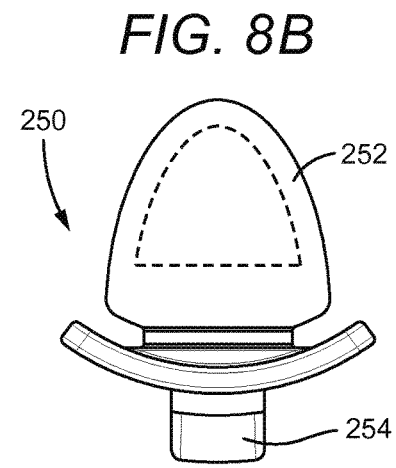
Figure 8C:
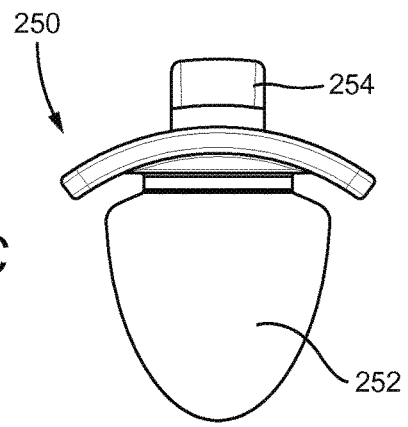
Figure 8D:
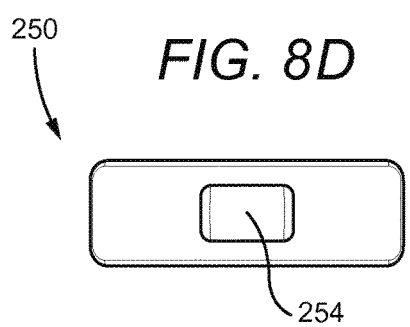
Figure 8E:
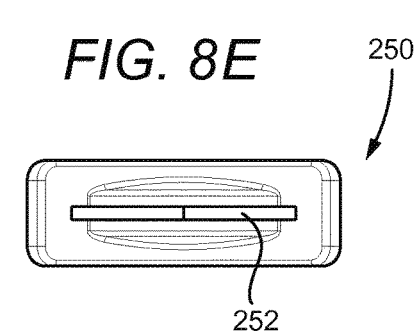
Figure 8F:
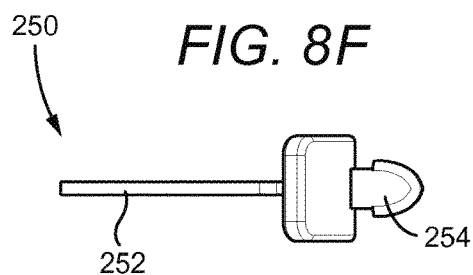
Figure 8G:
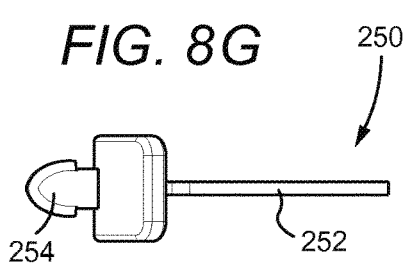

As best shown in FIG. 2H, the elbow 230 has a relatively thin cross-section and includes a seat 244 upon which the AAV 250 can sit. The seat 244 prevents over-deflection of the flap portion 252 of the AAV 250, e.g., prevents the flap portion 252 from deflecting too far towards the second portion 234 of the elbow 230. In addition, the seat 244 prevents edges of the flap portion 252 from getting caught in the elbow 230, e.g., prevents edges of the flap portion 252 from getting caught against rough surfaces or flash in the elbow 230.

1.2 Support Member

As shown in FIGS. 2A to 2H, 4A to 4J, and 8A to 8G, the support member 270 interlocks with the AAV 250 to provide a sub-assembly that is removably attached to the elbow 230 with a snap-fit. Specifically, the AAV 250, e.g., constructed of flexible silicone or other elastic material, includes an arrowhead-shaped protrusion 254 that removably interlocks with a slot 272 provided on the support member 270, e.g., constructed of rigid plastic. The inside edges of the slot 272 may have a filleted, curved, chamfered, or tapered configuration to facilitate assembly of the AAV 250.

Also, the slot 272 of the support member 270 and the protrusion 254 on the AAV 250 are relatively narrow to prevent mis-assembly, e.g., the flap portion 252 of the AAV 250 cannot be assembled through the slot 272.

The support member 270 includes two recesses 274 that interlock with respective tabs 242 provided to the elbow 230. As shown in FIGS. 2A to 2H, the elbow 230 is structured such that, when the support member 270 is attached to the elbow 230, the support member 270 includes portions that are substantially flush with a surface surrounding the port 240.

The support member 270 includes extended edges or wings 276 that protrude outwardly from the elbow 230 when assembled thereto. The wings 276 provide easy location and removal of the support member 270 on disassembly. In addition, the wings 276 provide a lead-in for press-fitting the support member 270 on assembly.

The support member 270 includes a central vertical rib 278. As illustrated, the rib 278 has an extended height and a contour that substantially matches an outer surface 246 of the elbow. The rib 278 prevents assembly of the support member 270 if the flap portion 252 of the AAV 250 gets caught against the elbow 230 on assembly. Specifically, when the support member 270 is assembled to the elbow 230, the rib 278 is located against the elbow outer surface 246, e.g., flush against the elbow outer surface, to prevent the AAV 250 from being assembled between the support member 270 and the elbow 230. For example, if the support member 270 is assembled to the elbow 230 with the AAV 230 in an incorrect orientation (e.g., the flap portion 252 of the AAV 250 positioned between the rib 278 and the elbow outer surface 246), the rib 278 prevents the support member 270 from interlocking with the elbow 230. It would then be evident to a user that the AAV had not been correctly installed.

The rib 278 may also prevent the support member 270 from being assembled to other elbow embodiments, e.g., the elbow 330 described below.

In an embodiment, the support member 270 has a thickness of about 1.5 mm. However, other thicknesses are possible.

2. Second Illustrated Embodiment of Elbow Assembly

FIGS. 5A to 5I illustrate an elbow assembly 318 according to another embodiment of the present invention. In the illustrated embodiment, the elbow assembly 318 is adapted for use with a nasal mask system of the type described in PCT Application No. PCT/AU2006/000770, filed Jun. 6, 2006, which claims priority to U.S. Provisional Application Nos. 60/687,453, 60/702,582, and 60/795,562, and PCT Application No. PCT/AU04/01832, filed Dec. 24, 2004, which are each incorporated herein by reference in its entirety. However, the elbow assembly 318 may be implemented into other mask systems, e.g., full-face mask, mouth mask, or a nasal mask.

The main components of the elbow assembly 318 are an elbow 330 (see FIGS. 6A to 6H), an anti-asphyxia valve (AAV) 250 (see FIGS. 8A to 8G), and a support member 370 to secure the AAV 250 to the elbow 330 (see FIGS. 7A to 7H). As noted above, the AAV 250 is a common component that may be used in both elbow assemblies 218, 318.

2.1 Elbow

As shown in FIGS. 6A to 6H, the elbow 330 includes a first portion 332 connectable to a mask frame and a second portion 334 connectable to an air delivery tube. The first portion 332 of the elbow 330 is releasably connected to a flanged collar member provided to the mask frame in a snap-fit manner as is known from U.S. Patent Application Publication No. 2003/0196656, which is incorporated herein by reference in its entirety.

The elbow 330 also includes a slot 338 to receive the AAV 250, a port 340 that is selectively closed by the flap portion 252 of the AAV 250 (depending on the presence of pressurized gas), and two retaining features 342, e.g., recesses or protrusions, for attaching the support member 370 with a snap-fit. As illustrated, the port 340 has a central rib 341 to prevent small objects from falling in or being placed in the port 340 and thereby affecting AAV function.

2.2 Support Member

As shown in FIGS. 5A to 5I, 7A to 7H, and 8A to 8G, the support member 370 interlocks with the AAV 250 to provide a sub-assembly that is removably attached to the elbow 330 with a snap-fit. Specifically, the AAV 250, e.g., constructed of flexible silicone or other elastic material, includes an arrowhead-shaped protrusion 254 that removably interlocks with a slot 372 provided on the support member 370, e.g., constructed of rigid plastic. The inside edges of the slot 372 may have a filleted, curved, chamfered, or tapered configuration to facilitate assembly of the AAV 250.

Also, the slot 372 of the support member 370 and the protrusion 254 on the AAV 250 are relatively narrow to prevent mis-assembly, e.g., the flap portion 252 of the AAV 250 cannot be assembled through the slot 372.

The support member 370 includes two tabs 374 that interlock with respective retaining features 342 provided to the elbow 330. The support member 370 also includes slightly extended edges 376. The edges 376 provide easy location and removal of the support member 370 on disassembly.

Also, the support member 370 has a relatively thin cross-section to allow easier deflection as the support member 370 is removed by un-wrapping the support member 370 from the elbow 330. In an embodiment, the support member 370 has a thickness of about 1.35 mm. However, other thicknesses are possible.

In addition, the support member 370 includes recessed sides 380 and a central vertical rib 378 integrally molded with the support member 370. When the support member 370 is assembled to the elbow 330, the recessed sides 380 and central vertical rib 378 are located against the elbow outer surface 346, e.g., flush against the elbow outer surface, to prevent the AAV 250 from being assembled between the support member 370 and the elbow 330.

3. AAV

FIGS. 8A to 8G illustrate the AAV 250 that may be used with either elbow assembly 218, 318. As explained above, the AAV 250 includes an arrowhead-shaped protrusion 254 that removably interlocks with a slot 272, 372 provided on the support member 270, 370 and a flap portion 252 that selectively closes an elbow port 240, 340 (depending on the presence of pressurized gas).

Figure 9:
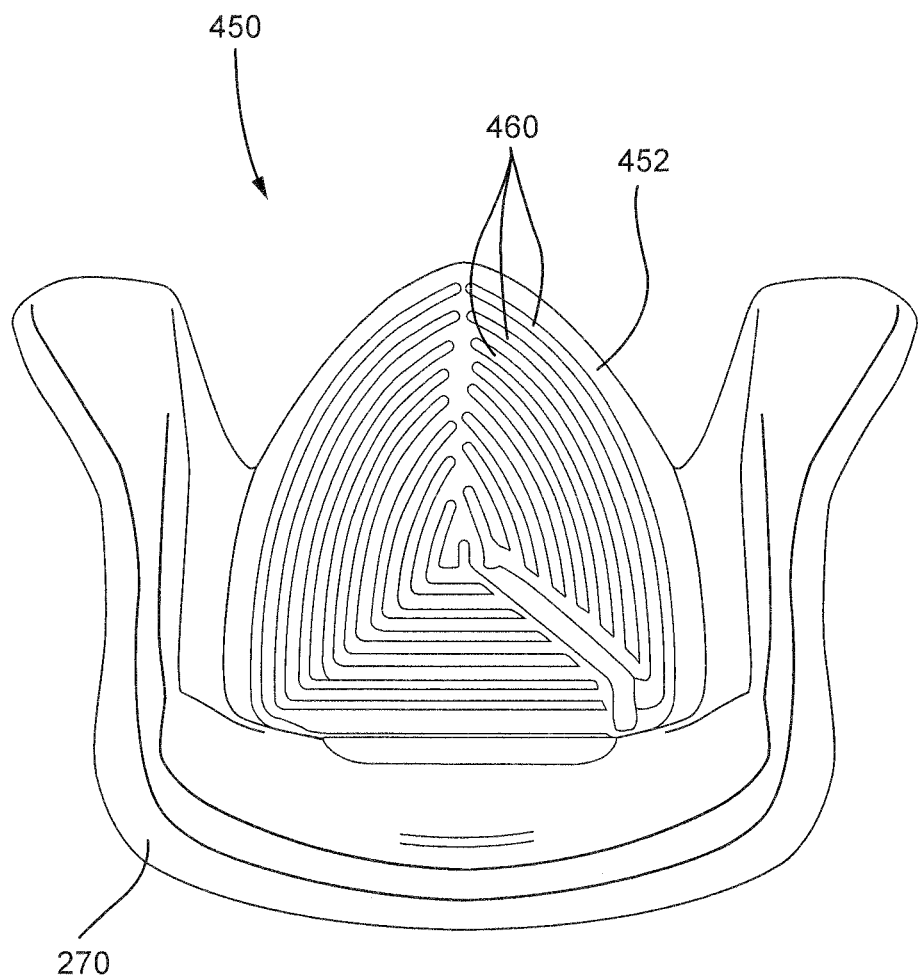
FIG. 9 shows an anti-asphyxia valve (AAV) attached to a support member according to another embodiment of the present invention.

FIG. 9 illustrates an alternative embodiment of an AAV 450 attached to the support member 270 shown in FIGS. 4A to 4J. As illustrated, the flap portion 452 of the AAV 450 includes an arrangement of protrusions and/or grooves 460 on its face.

4. Alternative Embodiment of Support Member

FIGS. 10A to 10G illustrate a support member 570 to secure an AAV to an elbow according to another embodiment of the present invention. The support member 570 is similar to the support member 270 described above. In contrast, the support member 570 includes one or more portions that have a textured or frosted surface.

As illustrated, the support member 570 includes a main body 571 and extended edges or wings 576 that protrude outwardly from the main body 571. Similar to clip 270, the support member 570 includes a slot 572 adapted to removably interlock with an AAV, two recesses 574 adapted to removably interlock with an elbow, and a central vertical rib 578 to prevent misassembly of the support member 570 to an elbow.

Figure 10A:
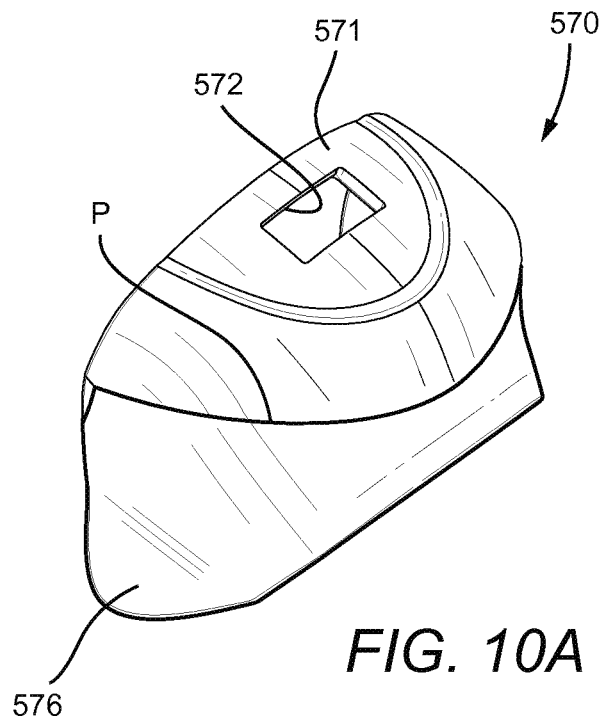
FIG. 10A to 10G show various views of a support member according to another embodiment of the present invention.
Figure 10B:
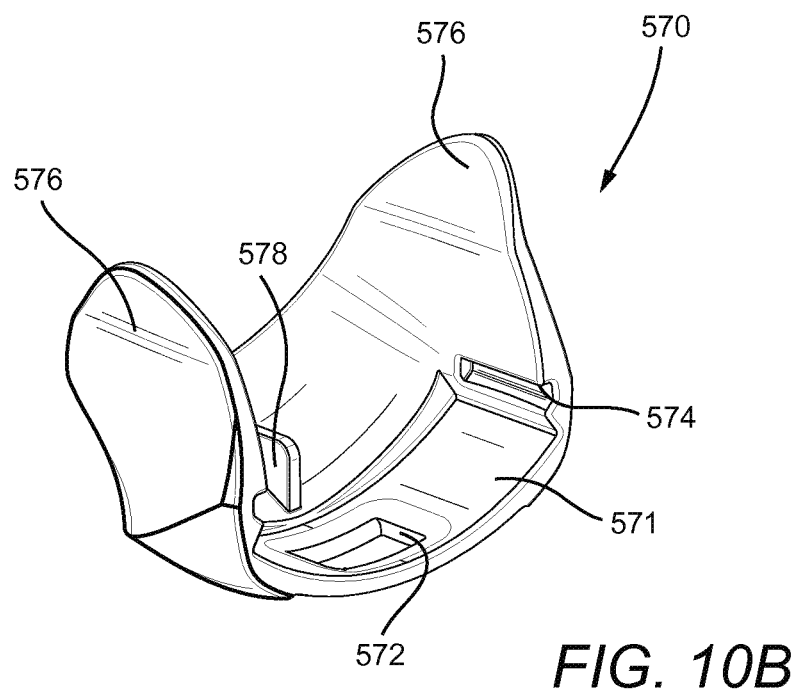
Figure 10C:
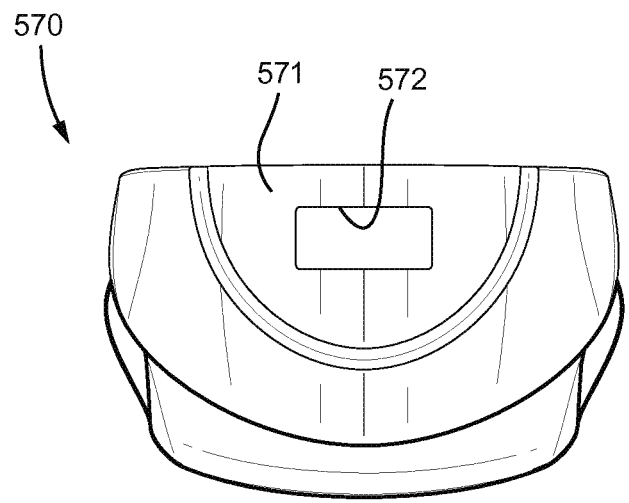
Figure 10D:
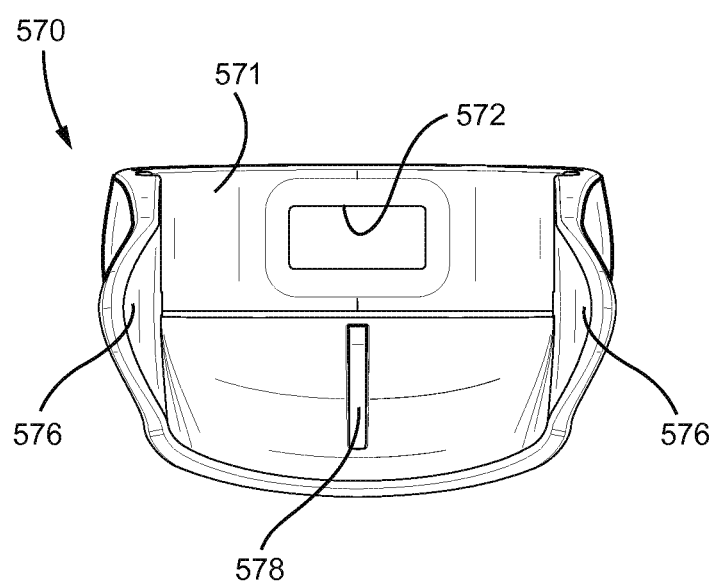
Figure 10E:
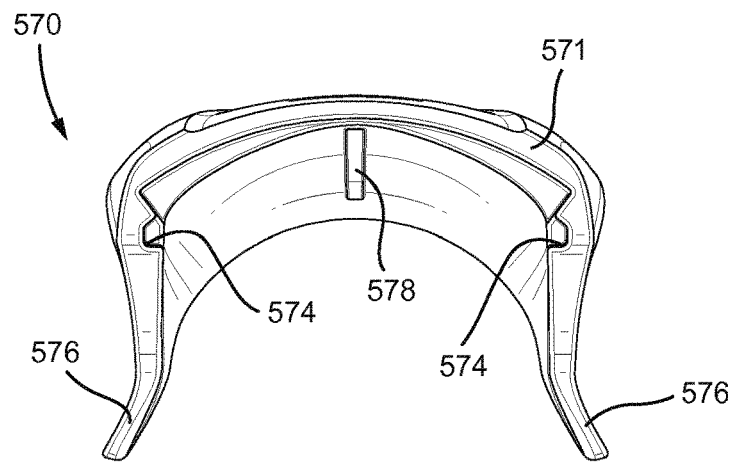
Figure 10F:
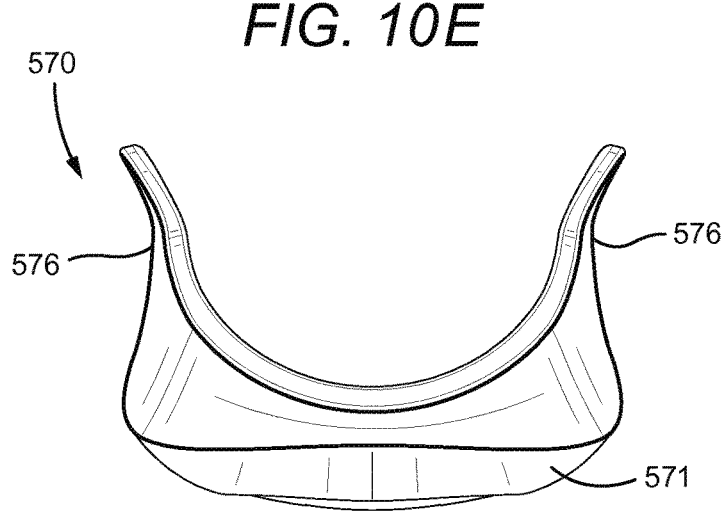
Figure 10G:
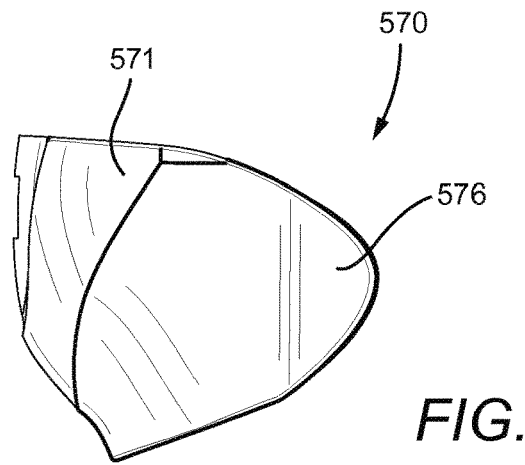

In the illustrated embodiment, the support member 570 includes a textured or frosted surface below a parting line P (see FIG. 10A). Specifically, a lower portion of the main body 571 and the wings 576 have a textured or frosted surface. The area including the textured or frosted surface is identified in darker outline in FIGS. 10A to 10D and 10F to 10G. As illustrated, the textured or frosted surface is provided to portions of the support member 570 that face outwardly from the elbow when the support member 570 is assembled thereto.

The textured or frosted surface is provided to improve grip of the support member 570 during assembly and disassembly with respect to the elbow. The textured or frosted surface also hides marks or imperfections on the support member 570 caused during manufacturing, e.g., injection molding gate marks, to improve aesthetics. In an embodiment, the textured or frosted surface may include any suitable surface treatment or surface roughening/scoring that improves grip.

It should be appreciated that the textured or frosted surface may be provided to any suitable portion of the support member 570. Also, a textured or frosted surface may be provided to other embodiments of a support member, e.g., support member 370.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:

1. An elbow assembly adapted to connect an air delivery tube to a mask assembly, the elbow assembly comprising:
   an elbow body with a first end, a second end and a bend between the first and second ends;
   a slot in a sidewall of the elbow body;
   an anti-asphyxia valve (AAV) assembly with a flap portion adapted to be received within the slot;
   a port on the sidewall of the elbow body adjacent the slot such that a portion of the sidewall of the elbow body intervenes between the slot and the port, the port being selectively closed by the flap portion; and
   a support member having an inside surface to which the flap portion is attached, the support member and the flap portion as a unit being attached to the elbow body,
   wherein the support member comprises an alignment member configured to cooperate with the elbow body to prevent assembly when the flap portion is misaligned with respect to the elbow body,
   wherein the support member is adapted to be flush with the port when secured to the elbow body, and
   wherein the support member is securable to the elbow body in only one orientation.

2. An elbow assembly according to claim 1, wherein the elbow body comprises a flange proximate the second end, and the support member is adapted to abut the flange when secured to the elbow body.

3. An elbow assembly according to claim 1, wherein only an outermost surface of the support member at one end of the support member is adapted to be flush with an outermost surface of the elbow body when the support member is secured to the elbow body.

4. An elbow assembly according to claim 1, wherein the support member comprises grip members that protrude outward from the elbow body when the support member is clipped to the elbow body.

5. An elbow assembly according to claim 1, wherein the alignment member is adapted to cooperate with the elbow body to prevent the support member from being secured to the elbow body when the flap portion is misaligned with the support member.

6. An elbow assembly according to claim 1, wherein the port is upstream of the slot.

7. An elbow assembly according to claim 1, wherein the support member is configured to be removably secured to the elbow body.

8. An elbow assembly according to claim 1, wherein the AAV assembly is configured to be removably secured to the support member.

9. An elbow assembly according to claim 1, wherein at least part of the support member engages the elbow body at the bend.

10. An elbow assembly according to claim 1, wherein the elbow assembly further comprises a member configured to prevent over-deflection of the flap portion through the port.

11. An elbow assembly according to claim 1, wherein the flap portion comprises a flexible silicone or other elastic material.

12. An elbow assembly according to claim 1, wherein the elbow body comprises a flange proximate the second end, and the support member is adapted to abut the flange when secured to the elbow body,
   wherein only an outermost surface of the support member at one end of the support member is adapted to be flush with an outermost surface of the elbow body when the support member is secured to the elbow body,
   wherein the support member comprises grip members that protrude outward from the elbow body when the support member is clipped to the elbow body,
   wherein the alignment member is adapted to cooperate with the elbow body to prevent the support member from being secured to the elbow body when the flap portion is misaligned with the support member,
   wherein the port is upstream of the slot,
   wherein the support member is configured to be removably secured to the elbow body,
   wherein the AAV assembly is configured to be removably secured to the support member,
   wherein at least part of the support member engages the elbow body at the bend,
   wherein the elbow assembly further comprises a member configured to prevent over-deflection of the flap portion through the port, and
   wherein the flap portion comprises a flexible silicone or other elastic material.

13. An elbow assembly adapted to connect an air delivery tube to a mask assembly, the elbow assembly comprising:
   an elbow body with a first end attachable to a mask assembly, a second end attachable to a swivel connection and a bend between the first and second ends;
   an aperture in the elbow body, at least a portion of which is between the bend and the second end of the elbow body;
   an anti-asphyxia valve (AAV) with a flap portion that is received within the aperture;
   a port on the elbow body adjacent to the aperture and between the aperture and the first end, the port being configured to be selectively closed by the flap portion; and
   a clip member adapted to cover the aperture and secure the AAV to the elbow,
   wherein the clip member comprises grip members configured to guide the clip member as the clip member is press-fit onto the elbow body, the grip members projecting away from the elbow body when the clip member is secured to the elbow body,
   wherein the clip member is adapted to be flush with the port when secured to the elbow body, and
   wherein the clip member is securable to the elbow body in only one orientation.

14. An elbow assembly according to claim 13, wherein the grip members are configured to be pushed outward by the elbow body as the clip member is press-fit onto the elbow body.

15. An elbow assembly according to claim 13, wherein the elbow body comprises a flange at the second end, the flange being positioned so that the swivel connection and the clip member abut the flange on opposite sides of the flange.

16. An elbow assembly according to claim 13, wherein the clip member comprises an alignment member that cooperates with the flap portion to prevent the clip member from being secured to the elbow body when the flap portion is misaligned with the clip member.

17. An elbow assembly according to claim 13, wherein the port is upstream of the aperture.

18. An elbow assembly according to claim 13, wherein the clip member is configured to be removably secured to the elbow body.

19. An elbow assembly according to claim 13, wherein the AAV is configured to be removably secured to the clip member.

20. An elbow assembly according to claim 13, wherein the grip members are configured to be pushed outward by the elbow body as the clip member is press-fit onto the elbow body,
  wherein the elbow body comprises a flange at the second end, the flange being positioned so that the swivel connection and the clip member abut the flange on opposite sides of the flange,
  wherein the clip member comprises an alignment member that cooperates with the flap portion to prevent the clip member from being secured to the elbow body when the flap portion is misaligned with the clip member,
  wherein the port is upstream of the aperture,
  wherein the clip member is configured to be removably secured to the elbow body, and
  wherein the AAV is configured to be removably secured to the clip member.

21. A facial mask assembly configured to deliver pressurized gas to a patient, the mask assembly comprising:
  a frame;
  a cushion provided to the frame and adapted to form a seal with the patient's face; and
  an elbow assembly provided to the frame and adapted to be connected to an air delivery tube that delivers breathable gas to the patient, the elbow assembly comprising:
    an elbow body with a first end attachable to the mask assembly, a second end attachable to a swivel connection and a bend between the first and second ends;
    an aperture in the elbow body, at least a portion of which is between the bend and the second end of the elbow body;
    an anti-asphyxia valve (AAV) with a flap portion that is received within the aperture;
    a port on the elbow body adjacent to the aperture and between the aperture and the first end, the port being configured to be selectively closed by the flap portion; and
    a clip member having an inside surface to which the flap portion is attached, the clip member and the flap portion as a unit being attached to the elbow body,
  wherein the clip member comprises an alignment member configured to cooperate with the elbow body to prevent assembly when the flap portion is misaligned with respect to the elbow body
  wherein the clip member comprises grip members configured to guide the clip member as the clip member is press-fit onto the elbow body, the grip members projecting away from the elbow body when the clip member is secured to the elbow body,
  wherein the clip member is adapted to be flush with the port when secured to the elbow body, and
  wherein the clip member is securable to the elbow body in only one orientation.

22. A mask assembly according to claim 21, wherein the elbow assembly further comprises a flange and a swivel connection at the second end, the swivel connection abutting the flange.

23. A mask assembly according to claim 22, wherein the clip member and the swivel connection abut the flange on opposite sides of the flange.

24. A mask assembly according to claim 21, wherein the grip members are configured to be pushed outward by the elbow body as the clip member is press-fit onto the elbow body.

25. A mask assembly according to claim 21, wherein the port is upstream of the aperture.

26. A mask assembly according to claim 21, wherein the clip member is configured to be removably secured to the elbow body.

27. An elbow assembly according to claim 21, wherein the AAV is configured to be removably secured to the clip member.

28. A mask assembly according to claim 21, wherein the elbow assembly further comprises a flange and a swivel connection at the second end, the swivel connection abutting the flange,
  wherein the clip member and the swivel connection abut the flange on opposite sides of the flange,
  wherein the grip members are configured to be pushed outward by the elbow body as the clip member is press-fit onto the elbow body,
  wherein the port is upstream of the aperture,
  wherein the clip member is configured to be removably secured to the elbow body, and
  wherein the AAV is configured to be removably secured to the clip member.

* * * * *